United States Patent
Nieminen et al.

(10) Patent No.: US 7,782,358 B2
(45) Date of Patent: Aug. 24, 2010

(54) MEASURING HUMAN MOVEMENTS—METHOD AND APPARATUS

(75) Inventors: Heikki V. Nieminen, Helsinki (FI); Jorma Kallio, Helsinki (FI)

(73) Assignee: Nokia Corporation, Espoo (FI)

( * ) Notice: Subject to any disclaimer, the term of this patent is extended or adjusted under 35 U.S.C. 154(b) by 391 days.

(21) Appl. No.: 11/760,375

(22) Filed: Jun. 8, 2007

(65) Prior Publication Data

US 2008/0306412 A1 Dec. 11, 2008

(51) Int. Cl.
*H04N 7/18* (2006.01)
*H04N 5/262* (2006.01)
*A61B 5/103* (2006.01)

(52) U.S. Cl. .......................... 348/77; 348/239; 600/595

(58) Field of Classification Search ................. 600/595, 600/300, 587; 348/77, 239; 73/865.4
See application file for complete search history.

(56) References Cited

U.S. PATENT DOCUMENTS

| | | | | |
|---|---|---|---|---|
| 4,655,227 A | * | 4/1987 | Gracovetsky | 600/595 |
| 4,813,436 A | * | 3/1989 | Au | 600/595 |
| 5,904,484 A | * | 5/1999 | Burns | 473/131 |
| 2005/0223799 A1 | * | 10/2005 | Murphy | 73/510 |
| 2006/0241521 A1 | * | 10/2006 | Cohen | 600/595 |
| 2007/0135225 A1 | * | 6/2007 | Nieminen et al. | 473/131 |
| 2008/0252445 A1 | * | 10/2008 | Kolen | 340/539.16 |

* cited by examiner

*Primary Examiner*—Jason Whipkey
(74) *Attorney, Agent, or Firm*—Ditthavong Mori & Steiner, P.C.

(57) ABSTRACT

A method and apparatus are disclosed for measuring human movement of a test subject during a standard coordination and balance test. The test subject is placed in a selected test position, e.g. standing on one leg for a selected test period. A sensor device is attached to at least one body member of the test subject. The sensor generates and transmits a signal representative of movement of the body member during the test (hereinafter "the test"). The test subject is viewed through a viewfinder of a visual recorder. The recorder and sensor device are activated and generate image and sensor signals which are transmitted to an analyzer for determining the movement of the body members during the test. A coordination and balance score is calculated from the test based on the body movement, body member location and test time. The score is compared a standard associated with the test, and provides an indicator of the test subject's coordination and balance skill.

35 Claims, 5 Drawing Sheets

MEASURING HUMAN MOVEMENTS—METHOD AND APPARATUS

BACKGROUND

1. Field

Embodiments of the invention relate to human movement measurement and analysis.

2. Description of Related Art

Apparatus and methods that provide feedback regarding a person's physical activities are divided into three categories including; basic activities, aerobic activities and coordination activities.

Basic activities are measured with steps, walk distance and energy consumed. Improvements in basic activities are measured with a development of accumulated steps per a certain period (i.e. weeks, months.). Aerobic activities are measured in running distance, velocity and heart rate. Improvements in aerobic activity are measured as the maximal oxygen intake. Coordination activities are measured as activity intensity and heart rate. Improvements in coordination are measured with coordination and balance tests.

The measurement of basic and aerobic activities is relatively straight forward for a test subject as compared to the measurement of coordination and balance skills. The latter involves capturing and measuring the amount of movement by different body members of a test subject during a physical test over a selected time period. Accordingly, what is needed in the art is an apparatus and method for capturing and measuring movement of different body members of a test subject during a physical test, wherein the apparatus and method are flexible for different coordination and balance skills and the test results are reproducible.

SUMMARY

The body members are equipped with sensor devices 104 which transmit a signal representative of the associated body member movement, should such occur during the coordination and balance test (hereinafter "test"). The sensor devices are taken from the group comprising standard accelerometers, magnetometers, angular rate sensors, gyroscope and the like. One or more of the sensor devices may be included in a game device, a mobile phone, a mobile communication device, an audio/video player, a position detecting device, and the like. Any movement signal(s) is transmitted as sensor data to a visual recording device 106, in one embodiment a portable video camera phone held by a photographer (not shown). In another embodiment, the recording device may be a stationary visual recording device with timing control. When the one or more sensor devices 104 are attached to the body member's information on which body member the sensor is attached is delivered or transmitted to an analyzing device. This may happen e.g. in a pairing phase between devices. Alternatively, when a specific test is selected in an analyzing device, also, information is given, e.g. on a display of the analyzing device, on which one or more body members one or more sensor devices should be placed. The sensor signals are transmitted by short-range communication protocols including Bluetooth® protocols, Infra-red Data Association (IrDA) protocols, Wireless Local Area Network (WLAN) protocols, UWB (Ultra Wide Band) protocols, and the like. The recorder 106 includes a processor, transceivers and the like which will be more fully described in conjunction with the description of FIG. 4 describing the processing of the sensor data for test results. In another embodiment the processor may be a separate standalone unit and not included in the recorder. Alternatively, the sensor device 104 may be a sticker having some specific color. One or more stickers can be attached to the limbs and torso of the body so that every sticker has its own color. Later, an analyzing program can detect the stickers with specific colors and analyze movement based on the sticker movements. Now, a specific color may mean a specific body member.

DESCRIPTION OF DRAWINGS

Embodiments of the invention will be further described in a Description of Embodiments taken in conjunction with appended drawings, in which:

FIG. 4A is a representation of software stored in a memory included in the analyzing terminal of FIG. 4 for managing the analyzer in the process of FIG. 1.

DESCRIPTION OF EMBODIMENTS

Figure 1:
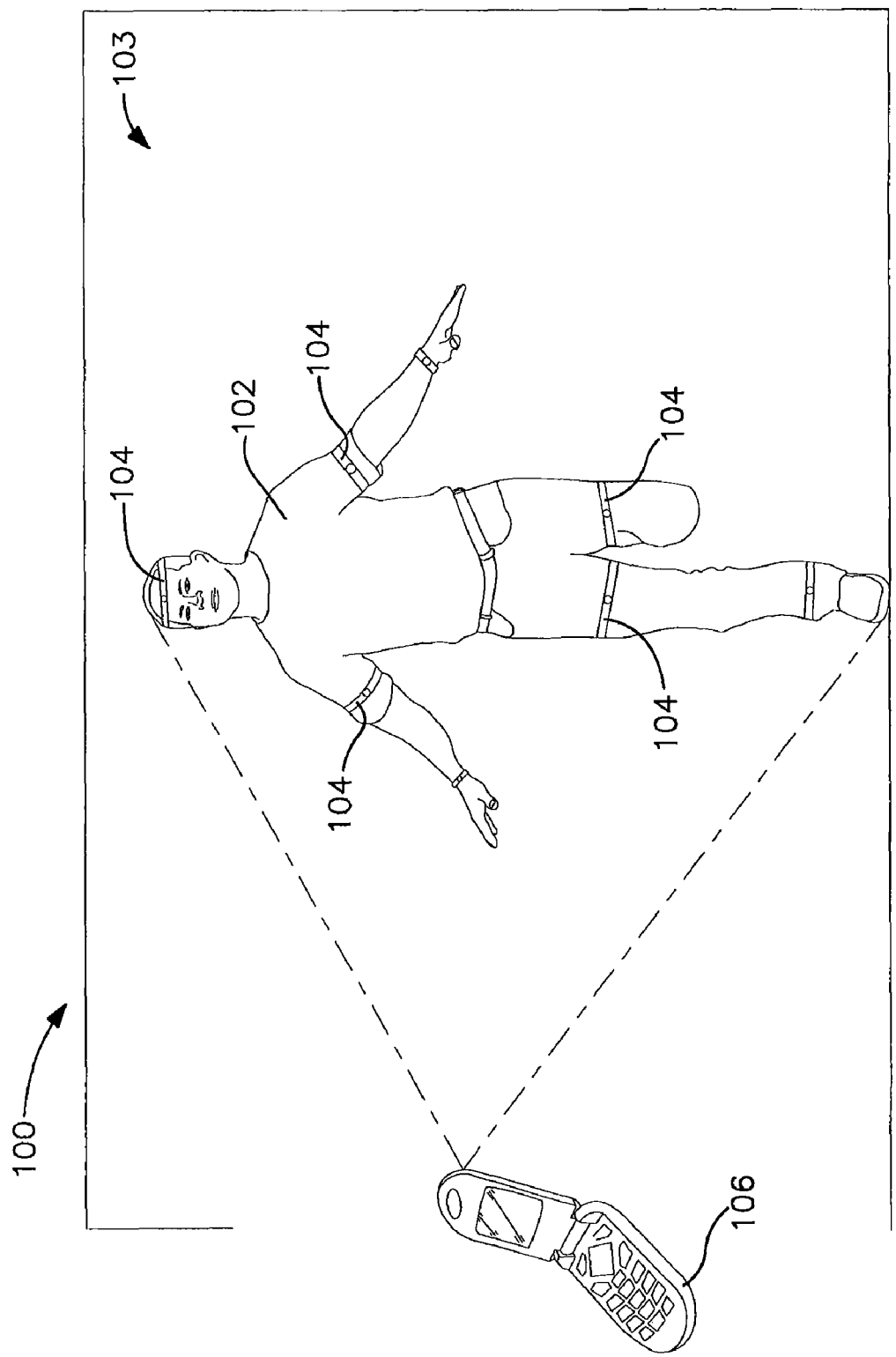
FIG. 1 is a representation of a testing process for a test subject including sensor devices in a test position captured by a visual recording device for measuring coordination and balance skill of the test subject and incorporating the principles of embodiments of the invention.

Referring to FIG. 1, depicting one aspect of the invention, a testing process 100 is shown being conducted to measure the coordination and balance of a human or test subject 102 for participating in sport activities or physical activities involving the risk of injury during a physical event. As defined in the Encyclopedia of Nursing, coordination is the capacity to move through a complex set of movements that requires rhythm, muscle tension, posture, and equilibrium. Coordination is generally measured by scoring the test subject's ability to perform the complex set of movements. Balance is the ability to maintain the center of gravity over the base of support, usually while in an upright position. Balance is measured by ability of the test subject to maintain balance, either statically or while performing various functional movements. The Berg Balance Scale (BBS) described in the Encyclopedia of Nursing is a recognizable tool for measuring balance.

The test subject 102 in FIG. 1 has assumed one of several test positions which may be used to measure coordination and balance based on the amount of movement of the test subject's body members, i.e. arms, legs, hands, torso and head during a test period. The test subject should be positioned in front of a plain background 103 for photographic reasons, as will become apparent hereinafter.

An apparatus, a method, and a non-transitory computer readable storage medium are provided. The computer readable storage medium carries one or more sequences of one or more instructions which, when executed by one or more processors, cause the apparatus to perform the method for measuring movement of different body members of a test subject during a test period, wherein the measurements provide an indication of coordination and balance skills of the test subject. The test is conducted by the test subject performing a series of physical activities, which may be static or dynamic. The movements of the test subject during the test are captured, measured and compared to standardized results for the activity as an indicator of the coordination and balance skills of the test subject. In one activity, the test subject assumes a test position, for example, standing on one leg while the other leg is raised. In another activity, the test subject may stand on one leg with hands in different positions. In still another activity, the test subject may stand on one leg with different torso positions or performing different hand movements with blinded eyes. During the test, a visual recording device, typically a video camera and communication device records the test subject movement in the test position during the test period. A template including an outline or cutout of the test position may be placed in the view finder of the recording device. The camera is operated to zoom the test subject within the cutout of the template during the test. The template may be placed in the recording device before or after capturing the image/video data. The template enables the captured image data to show the test subject's movement during the test. The image/video data is translated into signals representative of the movement by the test subject during the test and provided to a first analyzer. The test subject further includes sensory units attached to body members for generating signals indicative of the movement of the body members during the test. The sensor signals are captured and represent the movement of the body member associated with the sensor during the test. The sensor data is provided to a second analyzer. A processor having access to stored programs instructs the first analyzer and the second analyzer in calculating the amount of movement from the image/video signals and the sensor signals using the signal length or other signal parameter as a measure of the movement. A test score is calculated from the amount of movement and the test time. The test score is representative of the test subject's coordination and balance skill, and is compared to a standard developed from experiential data or a testing organization.

Figure 2A:
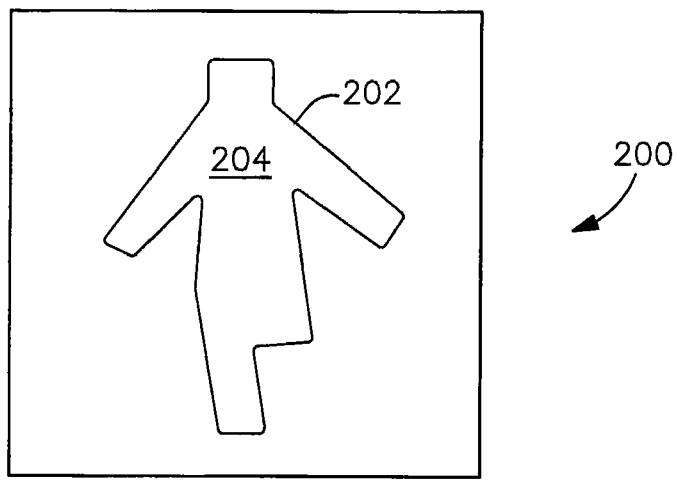
FIGS. 2A, B and C are representations of templates including an outline of a test subject in different test positions for use in the visual recording device of FIG. 1.
Figure 2B:
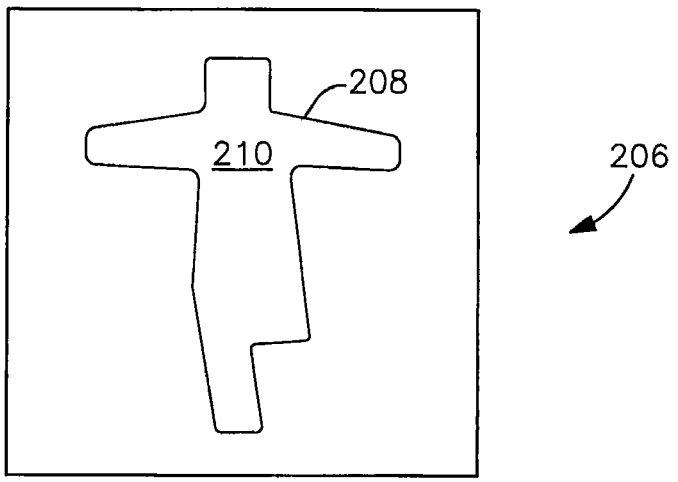
Figure 2C:
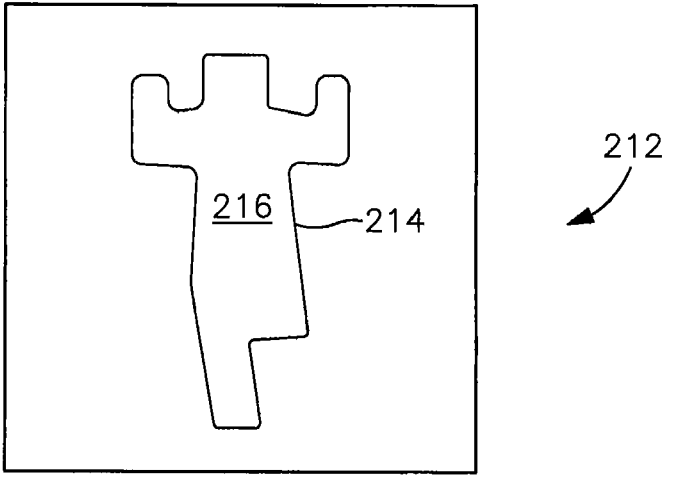

FIG. 2A, depicting one aspect of the invention, shows an example view in a standard viewfinder in the recorder 106. A template 200 is displayed in the viewfinder. The template includes an outline or cutout 202 of a test position 204 of the test subject 102 (see FIG. 1) standing on one leg with hands outstretched for balance, as shown in FIG. 1. FIG. 2B is another template 206 showing an outline 208 of the test subject in a test position 210 standing on one leg with the hands in different position from the hands in FIG. 2A. FIG. 2C is still another template 212 of the test subject showing an outline 214 in a test position 216 with hands extended with the test subject's eyes blinded by a cover (not shown). The templates may be installed in the viewfinder before the test subject's image is recorded or after the image is recorded by the recorder 106 (see FIG. 1).

Figure 3:
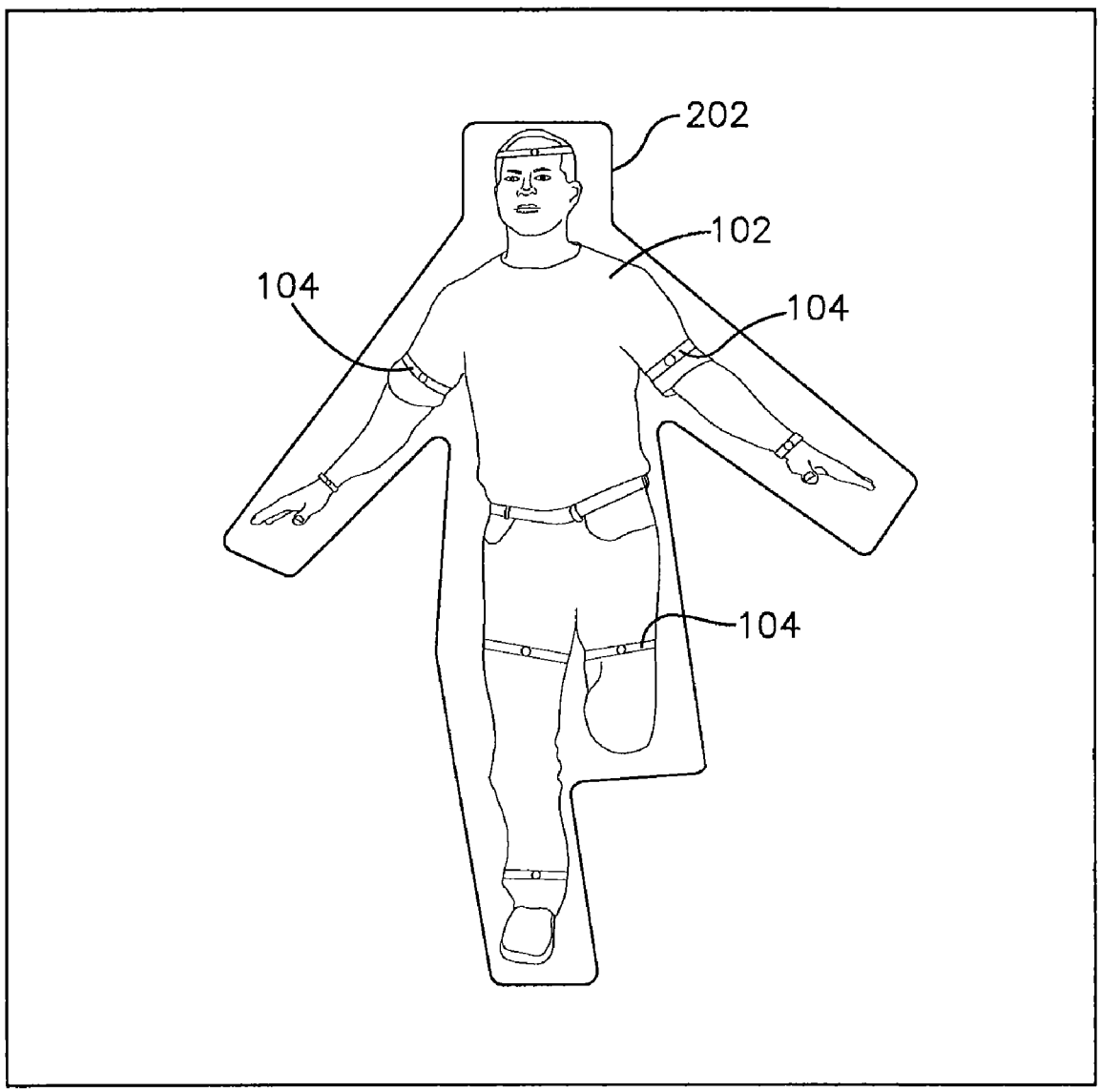
FIG. 3 is a representation of a viewfinder in the visual recording device of FIG. 1, the viewfinder displaying a template of FIG. 2A with the test subject displayed within the outline for use in determining the movement of body members of the test subject during a coordination and balance test.

In one embodiment shown in FIG. 3, the test subject 102 is viewed by the recorder 106 through the viewfinder (not shown) with the test subject within the outline or cutout 202 in the template 200 while the "test" is conducted over a test period. The visual movement(s) of the test subject's body members which overlap the outline 202 is detected by the recorder, in one embodiment a video recorder, and translated into electrical signals as image/video data representative of the movement of the body member. The image/video data may include a header assigned by the camera for identifying the body member. The image/video data is transmitted to an analyzer to be described in FIG. 4. The visual recorder may be a portable unit or a stationary standalone unit.

In an alternative embodiment of the invention, the test subject 102 is viewed by the recorder 106 through the viewfinder (not shown) without any outline or cutout 202 in the template 200 while the "test" is conducted over a test period. In this case, a virtual template is fitted over a starting image of the test subject in the analyzing process. Later, the result of the analyzing process is displayed with captured video with the test subject with the outline or cutout 202 in the template 200.

Figure 4:
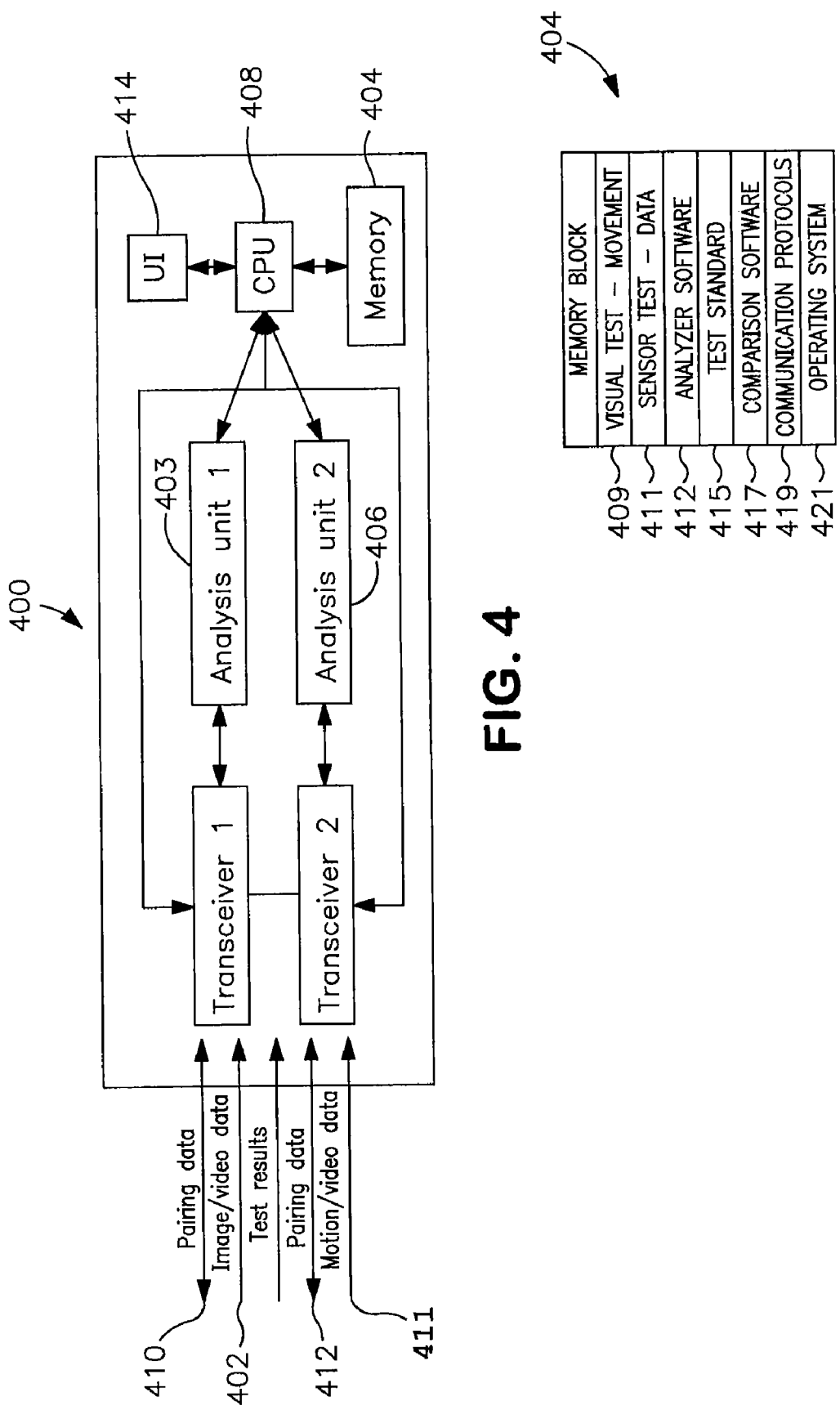
FIG. 4 is a representation of an analyzer linked to a processor for processing image movement signals representative of body part members' movements and sensor signals representative of body part members generated by the process of FIG. 1 and providing a combined test result for the coordination and balance skills of the test subject.

FIG. 4, depicting one aspect of the invention, discloses an analyzing unit 400 included in the recorder 106 (see FIG. 1) or in a standalone unit (not shown). Image/video data 402 is provided to an analyzer unit 403 via a transceiver 1 using short-range communication protocols when the analyzer is not within the recorder. The analyzer 400 includes a memory unit 404 containing data and program instruction shown in FIG. 4A for Visual Test Data—Movement 409; Sensor Test Data—Movement 411; Analyzer Software 412; Balance Test Standard 415; Comparison Software 417; Communication Protocols 419 and an Operating System 421. Alternatively, the analyzer 400 may be a separate device of sensor and recorder, like a personal computer or a network server.

The analyzer 400 translates electrical signals representative of image/video data into a movement measurement for a body member in terms of distance, where in one embodiment, the number of digital bits in the signal is representative of body member distance movement. The analyzer may use other parameters of the signal to measure movement. The amount of movement is used in the calculation of a coordination and balance score, where the balance score=f (amount_of_movement, time and body member location). The balance score can be compared to a standardized balance test or to a threshold as an indicator of the test subject's performance.

In like manner, sensor data 412 is provided to an analyzer unit 406 via transceiver 2 when the analyzer is not within the sensor device. The sensor data is processed into a movement distance for a body member serviced by a sensor unit. In some instances there may be adjacent analysis of image/video data and sensor data for a body member where movement is detected by both devices.

A CPU 408 is included in the analyzer for processing and providing the image/video 402 and sensor data 411 as pairing data 410 and 412. The image/video data 402 and the sensor data, as pairing data, maybe used in an external device (like 104 and 106) or other, e.g. mobile gaming device, pedometer, global positioning system (GPS) device paired with the recorder 106. The CPU also assembles the movement data and test results for presentation at a user interface 414. The interface may include a keyboard (not shown) to enable a user to select body members for test; test positions and the test period.

Figure 5:
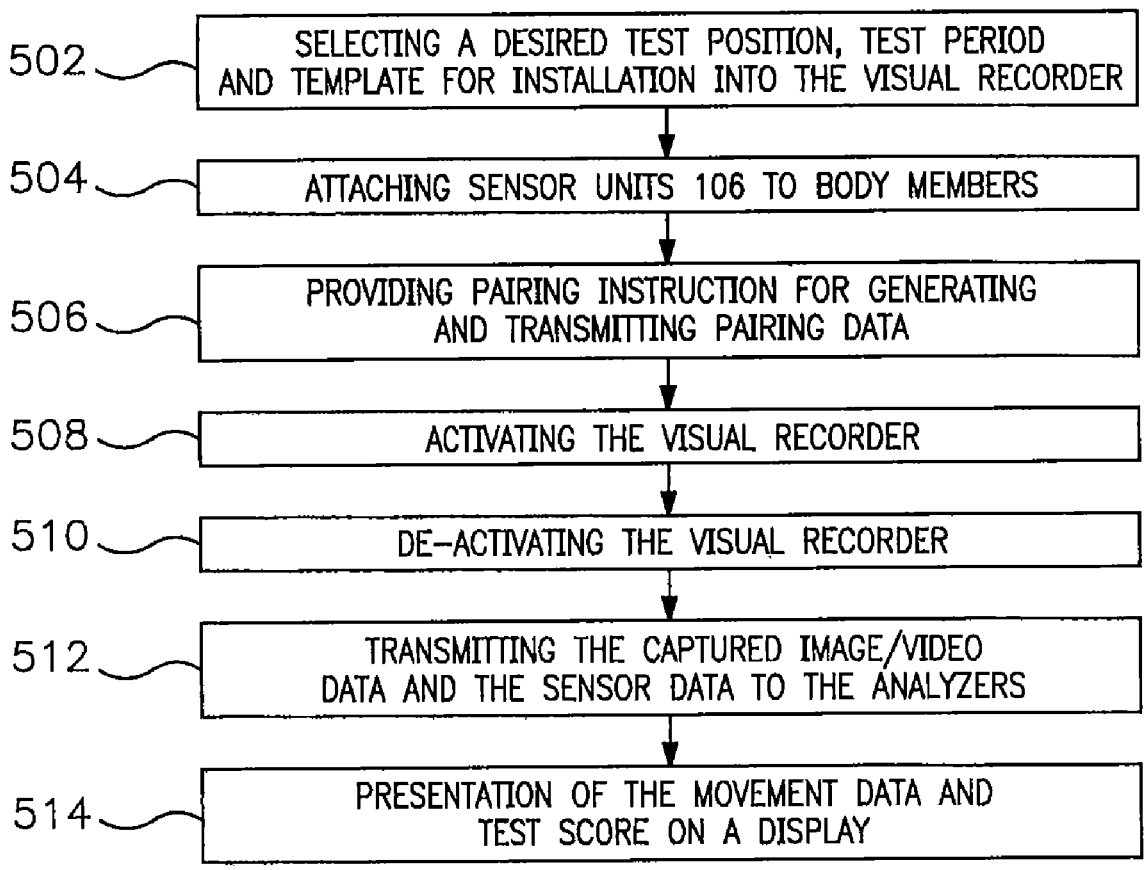
FIG. 5 is a flow diagram of the process of FIG. 1 in selecting test positions, generating, and displaying data representative of the movement of body members of the test subject during a coordination and balance test.

FIG. 5 is a flow diagram 500 of the test process 100 of FIG. 1, and includes operations, as follows:

502—Selecting a desired test position, test period and template for installation into the visual recorder via the user interface 414. Now information may be rendered on the selected test position to a user, e.g. on which body members the one or more sensor units 106 should be attached, e.g. in one use case, a mobile communication device with a motion sensor device in one of a test persons hand.

504—Attaching sensor units 106 to body members of the test subject 102.

506—Pairing of devices for providing the image/video data and the sensor data between the one or more sensor devices 104, one or more camera devices 106, and/or optional external analyzing device. Providing pairing instructions for generating and transmitting pairing data from the image/video data and the sensor data.

508—Activating the visual recorder e.g. by pressing a trigger to generate a recording signal enabling the visual recorder to capture image/video data of the test subject relative to the template during the test and substantially simultaneously sending a recording signal including a time stamp to activate the sensor devices to provide sensor data of body members during the test.

510—De-activating the visual recorder when the test period is complete and sending a signal with an end time stamp to de-activate the sensor devices.

512—Delivering the captured image/video data and the sensor data to the analyzers for processing into movement data of the test subject during the test and providing a test score of the coordination and balance skill of the test subject.

514—Presentation of the movement data and/or test score on a display in the interface unit.

While embodiments of the invention has been described, various changes can be made therein without departing from the spirit and scope of embodiments of the invention as defined in the appended claims, in which:

What is claimed is:

1. A method, comprising:
causing, at least in part, recording images of a test subject during a selected static balance test for a selected time period by visual recorder;
causing, at least in part, reception from at least one sensor attached to at least one body member of the test subject a signal representative of static balance of the body member during the test; and
analyzing image data of the images and sensor data of the signal to determine static balance of the test subject during the test by: aligning one test specific static balance position template over the test subject, and detecting positions of the body member of the test subject that overlap one outline of the position template during the test.

2. The method claim 1, further comprising:
including the template aligned in a viewfinder with the test subject during the test wherein the images of the test subject are recorded within the template and the at least one sensor is activated during the test.

3. The method of claim 1, further comprising: calculating a static balance score for the test subject during the test.

4. The method of claim 3, wherein the static balance score is calculated based upon at least an amount of movement, a time period and a body member location.

5. The method of claim 1, further comprising: comparing results of the test to a standard associated with the test.

6. The method of claim 1, further comprising: generating a signal to activate the at least one sensor.

7. The method of claim 6, causing, at least in part, installing a start time stamp in the signal; and causing, at least in part, transmission of the signal to activate the at least one sensor.

8. The method of claim 6, wherein causing, at least in part, installing a stop time stamp in the signal to deactivate the at least one sensor.

9. The method of claim 1, further comprising:
causing, at least in part, displaying of an analysis of static balance derived from the image and sensor data corresponding to the at least one body member of the test subject during the test.

10. The method of claim 1, further comprising:
causing, at least in part, transmission of the image and sensor data via at least one short-range communication protocol.

11. The method of claim 1, wherein the visual recorder is selected from the group consisting of a portable camera phone, a stationary time-controlled camera, a digital camcorder, and a digital camera.

12. The method of claim 1, wherein the sensor is selected from the group consisting of an accelerometer, an angular rate sensor, a gyroscope, and a magnetometer.

13. The method of claim 1, wherein a test position for a test subject is selected from the group consisting of standing on one leg, one leg standing with different hand positions, one leg standing with different torso positions, and one leg standing with different hand positions and eyes blinded.

14. The method of claim 1, further comprising: causing, at least in part, transmission of the image and sensor data via radio waves, infrared light, a wireless local area network (WLAN) link, or a combination thereof.

15. The method of claim 1, wherein the template is installed in a viewfinder after recording of the images.

16. The method of claim 1, wherein the test is the Berg Balance Scale (BBS).

17. An apparatus, comprising:
a visual recorder configured to record images of a test subject during a selected static balance test for a selected time period;
a receiver configured to receive from at least one sensor attached to at least one body member of the test subject a signal representative of static balance of the body member during the test;
an analyzer configured to analyze image data received from the visual recorder and sensor data received from the at least one sensor during the test by: aligning one test specific static balance position template over the test subject, and detecting positions of the at least one body member of the test subject that overlap one outline of the position template during the test; and
a processor configured to control the analyzer.

18. The apparatus of claim 17, wherein the visual recorder and the analyzer are located in a same device.

19. The apparatus of claim 17, wherein the sensor and the analyzer are located in a same device.

20. The apparatus of claim 17,
wherein said processor calculates a static balance score for the test subject during the test.

21. The apparatus of claim 17,
wherein said processor controls the analyzer in calculating static balance data of the test subject during the test thereby providing a test score for the test, and the processor compares results of the test to a standard associated with the test.

22. The apparatus of claim 17, wherein the processor or the visual recorder generates a signal to activate the at least one sensor.

23. The apparatus of claim 22, wherein the signal includes a start time stamp therein to activate the at least one sensor.

24. The apparatus of claim 22, wherein the signal includes a stop time stamp therein to deactivate the at least one sensor.

25. The apparatus of claim 17, further comprising:
a display configured to display an analysis of static balance derived from the image and sensor data corresponding to the at least one body member of the test subject during the test.

26. The apparatus of claim 17, further comprising
a transceiver configured to transmit the image and sensor data via at least one short-range communication protocol.

27. The apparatus of claim 17, wherein the visual recorder is selected from the group consisting of a portable camera phone, a stationary time-controlled camera, and a digital camera.

28. The apparatus of claim 17, wherein the sensor is selected from the group consisting of an accelerometer, an angular rate sensor, a gyroscope, and a magnetometer.

29. The apparatus of claim 17, wherein a test position for the test subject is selected from the group consisting of standing on one leg, one leg standing with different hand positions, one leg standing with different torso positions, and one leg standing with different hand positions and eyes blinded.

30. The apparatus of claim 17, further comprising:
a transceiver configured to transmit the image and sensor data via radio waves, infrared light, a wireless local area network (WLAN) link, or a combination thereof.

31. The apparatus of claim 17, wherein the template is installed in a viewfinder after recording of the images.

32. A non-transitory computer readable storage medium carrying one or more sequences of one or more instructions which, when executed by one or more processors, cause an apparatus to perform at least the following:
recording images of a test subject during a selected static balance test for a selected time period;
receiving from at least one sensor attached to at least one body member of the test subject a sensor signal representative of static balance of the body member during the test; and
analyzing image data of the images and sensor data of the signal to determine static balance of the test subject during the test by: aligning one test specific static balance position template over the test subject, and detecting positions of the body member of the test subject that overlap one outline of the position template during the test.

33. The computer readable storage medium of claim 32, wherein said test subject is positioned in a test position to measure coordination and balance skill of the test subject during the test for a selected time period, the test position is selected from the group consisting of standing on one leg, one leg standing with different hand positions, one leg standing with different torso positions, and one leg standing with different hand positions and eyes blinded.

34. An apparatus, comprising:
at least one processor; and
at least one memory including computer program code,
wherein the at least one memory and the computer program code configured to, with the at least one processor, cause the apparatus to perform at least the following:
record images of a test subject during a selected static balance test for a selected time period;
receive from at least one sensor attached to at least one body member of the test subject a sensor signal representative of static balance of the body member during the test; and
analyze image data of the images and sensor data of the signal to determine static balance of the test subject during the test by: aligning one test specific static balance position template over the test subject, and detecting positions of the body member of the test subject that overlap one outline of the position template during the test.

35. The apparatus of claim 34, wherein said test subject is positioned in a test position to measure coordination and balance skill of the test subject during the test for a selected time period, the test position is selected from the group consisting of standing on one leg, one leg standing with different hand positions, one leg standing with different torso positions, and one leg standing with different hand positions and eyes blinded.

* * * * *